(12) United States Patent
Thorson et al.

(10) Patent No.: US 7,264,686 B2
(45) Date of Patent: *Sep. 4, 2007

(54) METHOD OF FORMING A WAIST BAND ON AN ABSORBENT ARTICLE

(75) Inventors: Russell Evan Thorson, Appleton, WI (US); Paul VanGompel, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 402 days.

This patent is subject to a terminal disclaimer.

(21) Appl. No.: 10/734,843

(22) Filed: Dec. 12, 2003

(65) Prior Publication Data

US 2005/0126689 A1 Jun. 16, 2005

(51) Int. Cl.
*B32B 37/22* (2006.01)
*B32B 38/00* (2006.01)
*B32B 38/04* (2006.01)
*A61F 13/15* (2006.01)

(52) U.S. Cl. .................. 156/160; 156/164; 156/226; 156/229; 156/269; 156/299; 604/396

(58) Field of Classification Search ............... 156/160, 156/161, 163, 164, 166, 182, 229
See application file for complete search history.

(56) References Cited

U.S. PATENT DOCUMENTS 1,696,909 A 1/1929 Gillespie
2,166,012 A 7/1939 La Maida
2,544,620 A 3/1951 Steinert
2,748,772 A 6/1956 Titone et al.
2,749,912 A 6/1956 Teitler
3,098,484 A 7/1963 Younger
3,237,625 A 3/1966 Johnson
3,368,563 A 2/1968 Scheier
3,424,162 A 1/1969 Parravicini
4,319,572 A 3/1982 Widlund et al.
4,355,425 A 10/1982 Jones et al.
4,388,075 A 6/1983 Mesek et al.
4,615,695 A 10/1986 Cooper
4,762,521 A 8/1988 Roessler et al.

(Continued)

FOREIGN PATENT DOCUMENTS

EP 0 357 298 A2 3/1990

(Continued)

*Primary Examiner*—Melvin Mayes
(74) *Attorney, Agent, or Firm*—Thomas J. Connelly; David J. Arteman (57) ABSTRACT

A method of forming a waist band on an absorbent article is disclosed. The method includes forming stretchable front and back panels and attaching an elastic band to at least one of the panels. Each elastic band is cantilevered outward from a distal end of the panel to which it is attached. An absorbent assembly is also secured between the front and back panels. The method further includes folding one panel over the other panel so that the outer ends of the elastic bands are aligned approximately even to one another. The first and second side edges of the front panel, back panel and elastic bands are then joined together by a pair of seams to form an absorbent article having a waist opening and a pair of leg openings.

20 Claims, 5 Drawing Sheets

U.S. PATENT DOCUMENTS

| | | | |
|---|---|---|---|
| 4,850,989 A | 7/1989 | Villez | |
| 4,909,804 A | 3/1990 | Douglas, Sr. | |
| 4,938,754 A | 7/1990 | Mesek | |
| 4,968,312 A | 11/1990 | Khan | |
| 5,004,466 A | 4/1991 | Uda et al. | |
| 5,204,997 A | 4/1993 | Suzuki et al. | |
| 5,545,158 A * | 8/1996 | Jessup | 604/385.3 |
| 5,599,417 A | 2/1997 | Glaug et al. | |
| 5,624,424 A | 4/1997 | Saisaka et al. | |
| 5,735,839 A | 4/1998 | Kawaguchi et al. | |
| 5,879,500 A * | 3/1999 | Herrin et al. | 156/204 |
| 5,940,887 A | 8/1999 | Rajala et al. | |
| 5,968,031 A | 10/1999 | Schmitz | |
| 6,132,410 A | 10/2000 | Van Gompel et al. | |
| 6,217,563 B1 | 4/2001 | Van Gompel et al. | |
| 6,312,420 B1 | 11/2001 | Sasaki et al. | |
| 6,313,372 B1 | 11/2001 | Suzuki | |
| 6,358,350 B1 * | 3/2002 | Glaug et al. | 156/204 |
| 6,364,863 B1 | 4/2002 | Yamamoto et al. | |
| 6,551,430 B1 | 4/2003 | Glaug et al. | |
| 6,743,321 B2 * | 6/2004 | Guralski et al. | 156/250 |
| 6,755,808 B2 | 6/2004 | Balogh et al. | |
| 6,979,380 B2 * | 12/2005 | Thorson et al. | 156/259 |
| 7,008,497 B2 * | 3/2006 | Nakakado et al. | 156/229 |
| 7,018,369 B2 * | 3/2006 | VanGompel et al. | 604/396 |
| 7,108,759 B2 * | 9/2006 | You et al. | 156/73.1 |
| 2002/0128617 A1 | 9/2002 | Roe et al. | |
| 2002/0152540 A1 | 10/2002 | Van Gompel et al. | |
| 2003/0088230 A1 | 5/2003 | Balogh et al. | |
| 2003/0125690 A1 | 7/2003 | Hermansson et al. | |
| 2004/0045924 A1 | 3/2004 | Naritomi et al. | |
| 2004/0082933 A1 | 4/2004 | Karami | |
| 2004/0116887 A1 | 6/2004 | Thorson et al. | |
| 2004/0122400 A1 | 6/2004 | Hancock-Cooke et al. | |
| 2004/0122404 A1 | 6/2004 | Meyer et al. | |
| 2004/0122405 A1 | 6/2004 | Van Gompel et al. | |
| 2004/0122411 A1 | 6/2004 | Hancock-Cooke | |
| 2004/0210205 A1 | 10/2004 | Van Gompel et al. | |
| 2004/0243085 A1 | 12/2004 | Veith et al. | |
| 2004/0243086 A1 | 12/2004 | Van Gompel et al. | |
| 2004/0243089 A1 | 12/2004 | Veith et al. | |
| 2005/0004549 A1 | 1/2005 | Maas et al. | |
| 2005/0020992 A1 * | 1/2005 | Van Gompel et al. | 604/385.01 |
| 2005/0107763 A1 | 5/2005 | Matsuda et al. | |
| 2005/0131385 A1 | 6/2005 | Sakaguchi | |

FOREIGN PATENT DOCUMENTS

| | | |
|---|---|---|
| EP | 0 404 648 A1 | 12/1990 |
| EP | 0 456 885 A1 | 11/1991 |
| EP | 0 460 467 A1 | 12/1991 |
| EP | 0 528 282 A2 | 2/1993 |
| EP | 96/08224 * | 3/1996 |
| EP | 1 072 243 A2 | 1/2001 |
| EP | 1 157 681 A2 | 11/2001 |
| EP | 1 184 017 A1 | 3/2002 |
| EP | 1 240 881 A2 | 9/2002 |
| EP | 1 374 814 A1 | 1/2004 |
| EP | 1 393 701 A2 | 3/2004 |
| EP | 1 428 487 | 6/2004 |
| GB | 2 253 131 A | 9/1992 |
| GB | 2 297 474 A | 8/1996 |
| JP | 03-195555 A | 8/1991 |
| JP | 03-205053 A | 9/1991 |
| JP | 04-089050 A | 3/1992 |
| JP | 04-354948 A | 12/1992 |
| JP | 11-318978 A | 11/1999 |
| JP | 2000-279447 A | 10/2000 |
| JP | 2003-339771 A | 12/2003 |
| JP | 2004-089403 A | 3/2004 |
| WO | WO96/08224 A2 | 3/1996 |
| WO | WO99/56688 A1 | 11/1999 |
| WO | WO 03/002052 A1 | 1/2003 |
| WO | WO 2004/054490 A1 | 7/2004 |

* cited by examiner

METHOD OF FORMING A WAIST BAND ON AN ABSORBENT ARTICLE

BACKGROUND OF THE INVENTION

Absorbent articles, like disposable absorbent undergarments, are designed for absorbing human exudate. Many disposable absorbent undergarments are similar in appearance, size and shape to a regular cloth underwear except that they are not designed to be laundered and reused two or more times. Disposable absorbent undergarments are sized and configured to be worn by humans of various ages, for example, infants, toddlers, and adults. Disposable absorbent undergarments are meant to be disposed of after being used once instead of being laundered or dry cleaned for re-use. Such absorbent undergarments are designed to be pulled up around the user's torso without having to first open the undergarment in order to place it on a person's body. The stretchability of the material used to construct the absorbent undergarment permits the undergarment to snugly conform to the anatomy of the user's torso. The absorbent undergarment can be manufactured to be an infant diaper, a child training pant, an adult incontinence garment, a feminine menstrual pant, etc.

Some disposable absorbent undergarments manufactured today resemble regular cloth underwear in that they have a waist opening and a pair of leg openings. Such disposable absorbent undergarments can be pulled up around the torso of a user in a similar fashion as regular cloth underwear. It has been found that a pant-like absorbent undergarment is generally more discreet than a refastenable absorbent undergarment because it does not contain the extra material forming the hook or adhesive fasteners and loop or adhesive landing zone materials. An absorbent undergarment tends to be sleeker, smoother and slimmer especially around the waist opening. For this reason, many adults suffering from incontinence tend to prefer the pant-like design. Today, the absorbent crotch portion of some absorbent undergarments tend to sag or droop once they fill up with a large quantity of body fluid, such as urine. As the crotch portion sags, an extra downward force is applied to the front and back panels that can cause the entire undergarment to slide downward on the user's torso. This creates an uneasy and uncomfortable feeling for the user. Therefore, there is a need for a disposable absorbent undergarment that contains a structure that will resist downward sliding on the user's torso.

Now a method of forming a waist band on an absorbent article, especially absorbent undergarments, has been invented. The elastic band creates a snug fit at the waist opening that prevents the undergarment from sliding downward on the user's torso as the absorbent crotch portion accumulates body fluid.

SUMMARY OF THE INVENTION

A method of forming a waist band on an absorbent article is disclosed. The method includes forming a stretchable front panel having a distal end, first and second side edges, and a retracted length measured between the first and second side edges. A stretchable back panel is also formed which has a distal end, first and second side edges, and a retracted length measured between the first and second side edges. An elastic band is attached to at least one of the front and back panels. Each of the elastic bands has first and second side edges and an outer end. Each elastic band is cantilevered outward from the distal end of the panel to which it is attached. Each elastic band has a retracted length that is less than the retracted length of the panel to which it is secured. An absorbent assembly is then secured between the front and back panels. The absorbent assembly includes a liquid pervious bodyside liner, a liquid-impervious outer cover, and an absorbent positioned therebetween. The method also includes folding the front panel over the back panel so that the outer end of one elastic band is aligned approximately even with the outer end of the other elastic band. The first and second side edges of the front panel, back panel and the elastic bands are then joined together by a pair of seams to form an absorbent article having a waist opening and a pair of leg openings.

DETAILED DESCRIPTION

Figure 1:
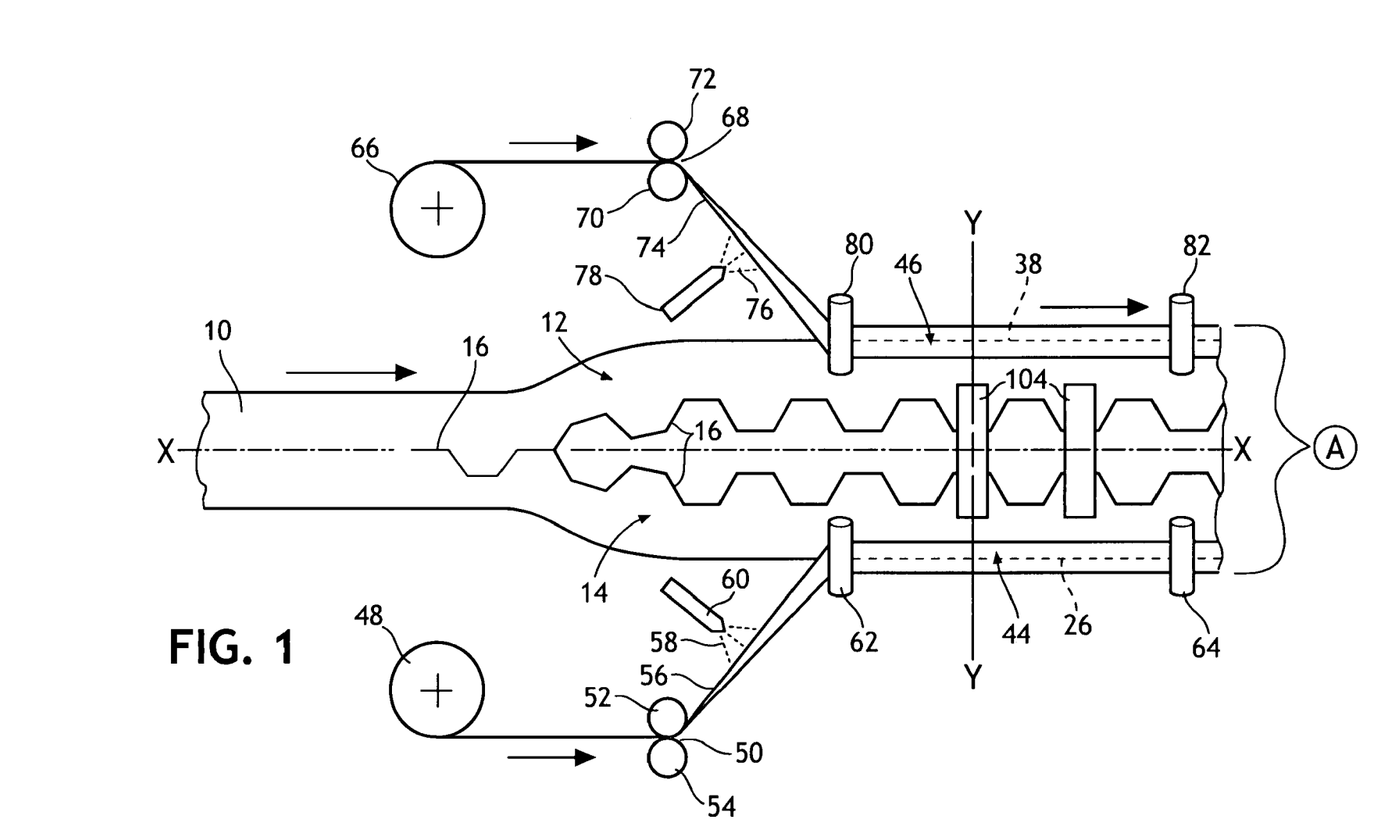
FIG. 1 is a schematic of a portion of the method of forming a waist band on an absorbent article wherein the elastic band is attached to at least one of the front and back panels prior to securement of an absorbent assembly.

Referring to FIG. 1, a schematic is shown of a portion of the method for forming a waist band on an absorbent article. The method begins by routing a stretchable material 10 in a machine direction, depicted as moving from left to right in FIG. 1. The stretchable material 10 can be an elastic material or an elastic laminate that contains two or more layers wherein at least one of the layers is elastic. By "layer" it is meant a single elastic sheet, an elastic film, an elastic net-like material or a plurality of elastic strands, threads or ribbons. When a plurality of elastic strands, threads or ribbons is utilized, they can be positioned between two or more outer layers.

The stretchable material 10 is capable of being elongated in at least one direction. Desirable, the stretchable material 10 is capable of being elongated in two or more directions when a force is applied, such as by pulling on the material. The stretchable material 10 can be made such that it has a predetermined amount of stretch. The actual amount of stretch can vary. The stretchable material 10 can be constructed such that it is capable of stretching in a range of from between about 10% to about 1,000%. Particular stretch values for the stretchable material 10 can be 10%, 25%, 50%, 100%, 200%, 300%, 500%, 1,000%, etc. Desirably, the range of stretch in the material 10 will range from about 25% to about 500%. More desirably, the range of stretch in the material 10 will range from about 50% to about 300%. Most desirably, the range of stretch in the material 10 will range from about 75% to about 200%. An example of a 100% stretch for a strip of material 1 inch (about 25.4 mm) long is an elongation to 2 inches (about 50.8 mm).

The stretchable material 10 is also capable of retracting to or towards its original pre-stretched length. By "retraction" it is meant that the material 10 can be shortened, or reduced in size or length. For example, a 1 inch (about 25.4 mm) strip of material can be stretched to 2 inches (about 50.8 mm) by applying a pulling force to each of its ends. When the force is removed, the material will retract to or towards its original pre-stretched length of 1 inch (about 25.4 mm).

The stretchable material 10 can be constructed from natural or synthetic fibers and can be a woven or non-woven material. The stretchable material 10 can be formed as a single layer, a double layer or from multiple layers with one of the inner layers being elastic. A stretch bonded laminate (SBL) is a good selection for the stretchable material 10 because it has good elastic properties, is commercially available and is reasonably priced. Exemplary SBL materials are described in U.S. Pat. No. 4,720,415, which is hereby incorporated by reference and made a part hereof. In the SBL material, the elastic core or middle layer is elongated before the two outer non-woven layers are attached. The attachment can be by an adhesive, by heat, by pressure, by a combination of heat and pressure, etc. Another material option for the stretchable material 10 is a necked bonded laminate (NBL). The NBL material is also a three layer laminate but the elastic core or middle layer is not pre-stretched prior to being attached to two outer non-woven layers. The outer layers are necked stretched before the elastic or middle layer is attached to them. Exemplary NBL materials are described in U.S. Pat. No. 5,336,545, which is hereby incorporated by reference and made a part hereof. Other examples of elastomeric materials that can be used for the stretchable material 10 include a continuous filament stretch bonded laminate (CFSBL), a vertical filament laminate (VFL), a necked stretch bonded laminate (NSBL), and a necked thermal laminate (NTL). Combinations of the above materials can also be used. Exemplary CFSBL materials are described in U.S. Pat. No. 5,385,775, which is hereby incorporated by reference and made a part hereof.

It should also be noted that the stretchable material 10 can be constructed from an elastic film that is capable of being stretched in at least one direction and desirably in both the machine direction and the cross-direction. Alternatively, the stretchable material 10 can be an elastic nonwoven that has a machine direction stretch or a cross-direction stretch. Extensible materials can also be used to form the stretchable material 10. Various other stretchable and elastic materials can be used which are known to those skilled in the art.

Alternatively, the stretchable material 10 can be formed from two outer layers with a plurality of elastic strands sandwiched therebetween. The elastic strands can be formed from LYCRA. LYCRA is a registered trademark of E. I. Du Pont De Nemours & Co., having an office at 1007 Market Street, Wilmington, Del. 19898. The elastic strands can be aligned approximately parallel to one another or be angled or skewed relative to one another. The elastic strands can also be uniformly or randomly spaced apart from one another. The elastic strands can vary in shape, size, configuration, and/or length. The diameter and/or cross-sectional configuration of the elastic strands, the decitex (weight in grams per 10,000 meters of a strand) of the elastic strands, and the tension imparted into the elastic strands can all be varied to suit one's particular product needs. The elastic strands can have a round, semi-circular, square, rectangular, oval or some other geometrical configuration. The elastic strands can overlap, intersect or crisscross at least one other elastic strand. The various ways of positioning, orienting, and adhering the elastic strands to the two outer layers are well known to those skilled in the art.

The stretchable material 10 can be "stretched to stop" if desired. By "stretched to stop" it is meant that the material can be elongated or lengthened to a point where any further pulling force exerted on it would either break the material or cause the material to become permanently deformed, such that it loses its ability to retract back to or towards its original length. It has been found that it is advantageous in many manufacturing processes to stretch an elastic carrier material to stop before one or more elastic bands or elastic segments are secured thereto. By doing so, a more uniform quality product can be manufactured.

Still referring to FIG. 1, the stretchable material 10 is shown having a longitudinal centerline X-X. The stretchable material 10 can be slit or cut approximate this longitudinal centerline X-X to form a first web 12 and a second web 14 when the two webs 12 and 14 are to be of approximately the same width, measured in the cross-direction along the Y-Y axis. When one web is required to be wider than the other web, the slit can be offset from the longitudinal centerline X-X. As shown, a longitudinally extending cut 16 is formed in the stretchable material 10. The cut 16 is shown having a serpentine configuration. However, the cut 16 can be formed with almost any geometrical shape that is desired. A straight line cut will suffice for some applications while an arcuate cut, a saw tooth cut, a winding cut, etc. may work well for unique product designs which incorporate leg openings, windows, etc. After the cut 16 is formed, the first web 12 and the second web 14 are moved away from one another into a spaced apart relationship. The first and second webs, 12 and 14 respectively, will form the front and back panels of a finished absorbent article 18, see FIG. 2.

Figure 2:
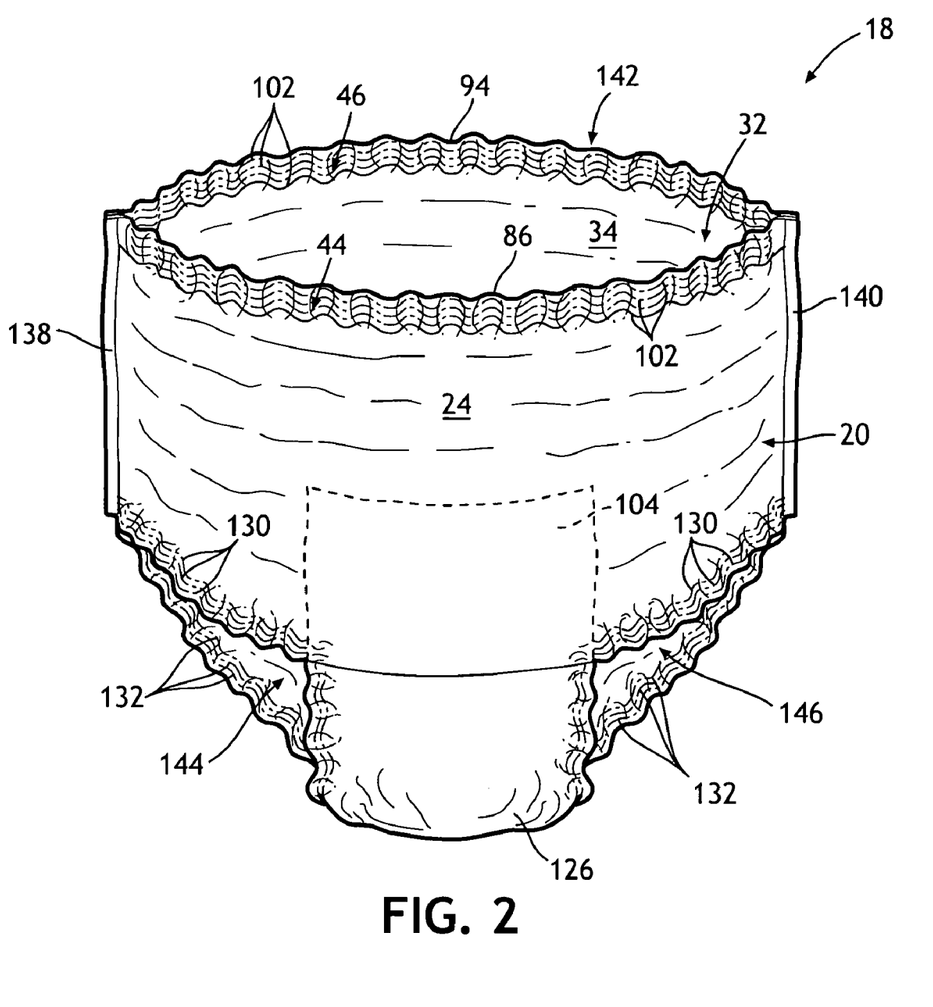
FIG. 2 is a perspective view of a disposable, pant-like absorbent article having an elastic band secured to the front and back panels and extending substantially around the entire waist opening.
Figure 3:
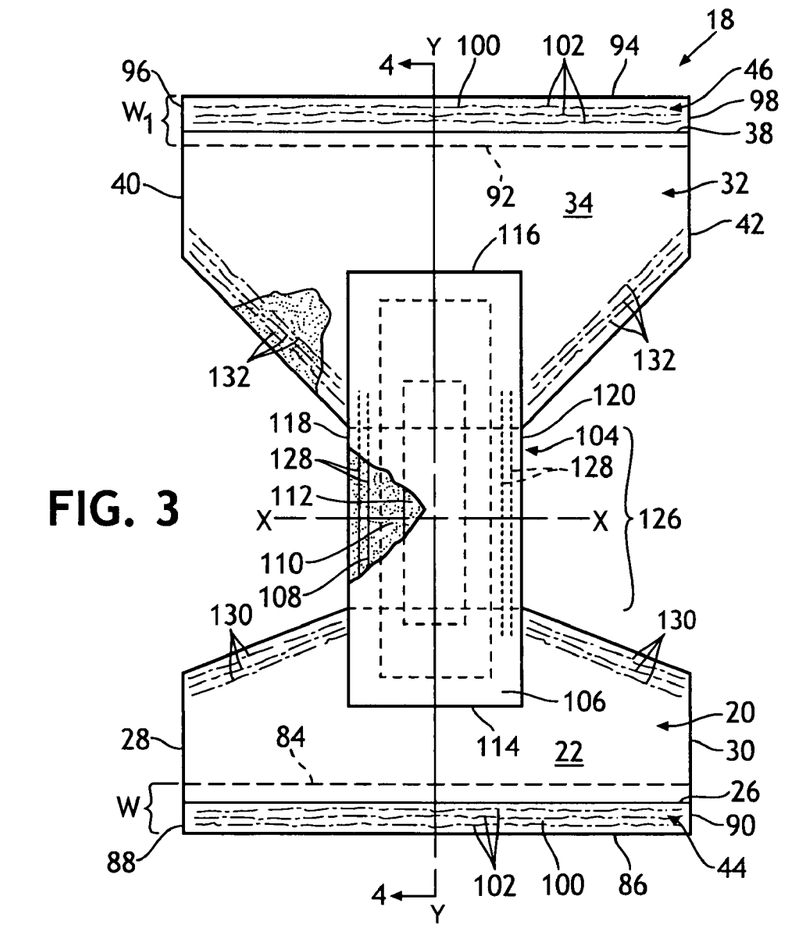
FIG. 3 is a plane view of the disposable, pant-like absorbent article shown in FIG. 2 depicting an absorbent assembly secured to the inner surface of the stretchable front and back panels and showing two partial cut away views of the construction of the absorbent assembly and the leg elastics.
Figure 4:
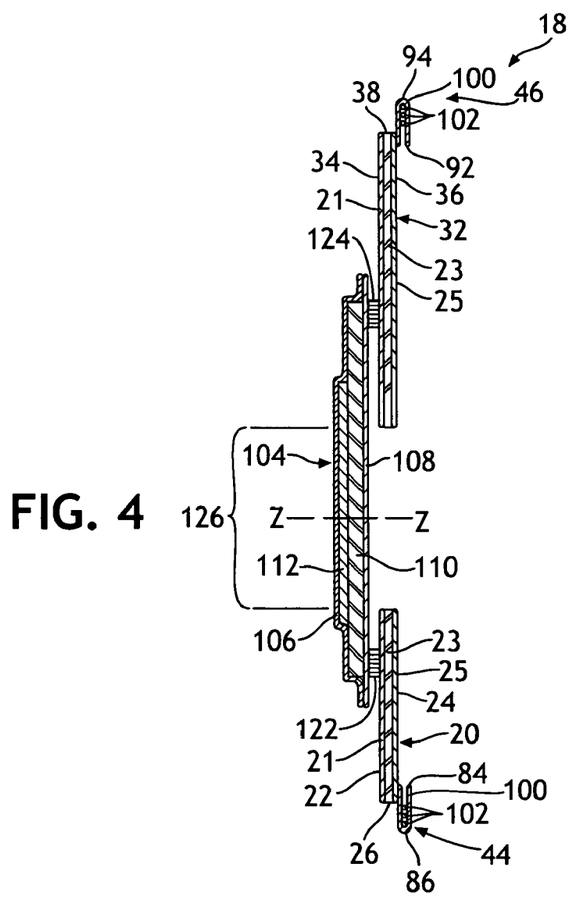
FIG. 4 is a side view of the disposable, pant-like absorbent article shown in FIG. 3 and taken along line 4-4.

Referring now to FIGS. 2-4, an absorbent article 18 is the form of a disposable, pant-like undergarment. The disposable, pant-like undergarment 18 is intended to be worn by persons, including infants, toddlers, or adults, and is designed for a single or temporary use. The disposable pant-like undergarment is meant to be disposed of after being used once instead of being laundered or dry cleaned for re-use. The disposable pant-like undergarment is designed to be pulled up around the user's torso without having to first open the undergarment in order to place it on a person's body.

In FIG. 2, the absorbent article 18 is shown as it would appear just prior to being pulled up around a user's torso. In FIGS. 3 and 4, the absorbent article 18 is depicted in an open position solely for the purpose of better showing the various components. In FIGS. 3 and 4, the open pant-like absorbent article 18 has a transverse central axis X-X that corresponds with the longitudinal centerline X-X shown in FIG. 1. The absorbent article 18 also has a longitudinal central axis Y-Y, and a vertical central axis Z-Z.

The absorbent article 18 includes a stretchable front panel 20 having an inner surface 22, an outer surface 24, a distal end 26, a first side edge 28 and a second side edge 30. The absorbent article 18 also includes a stretchable back panel 32 having an inner surface 34, an outer surface 36, a distal end 38, a first side edge 40 and a second side edge 42. The front and back panels, 20 and 32 respectively, are discontinuous from one another in the Y-Y direction. The inner-surfaces 22 and 34 of the front and back panels, 20 and 32 respectively, are in direct contact with the user's skin and are sometimes referred to as bodyside facing surfaces. The outer surfaces 24 and 36 are oppositely aligned to the inner surfaces 22 and 34 and are spaced away from the user's skin. The outer surfaces 24 and 36 are sometimes referred to as garment facing surfaces since they will be in direct contact with the inner surfaces of the user's outer clothing.

In FIG. 4, the front and back panels, 20 and 32 respectively, are formed from the stretchable material 10 described above. The stretchable material 10 is depicted as being constructed of three layers 21, 23 and 25. However, as noted above, the stretchable material 10 can consist of fewer than three layers or more than three layers, if desired. The absorbent article 18 also includes at least one, and desirably two, elastic bands 44 and 46. The elastic band 44 is attached to the front panel 20 and the elastic band 46 is attached to the back panel 32. It should be noted that only one elastic band, 44 or 46, can be utilized which can be attached either to the front or back panels, 20 and 32 respectively. In FIG. 4, the elastic bands 44 and 46 are shown being attached to the outer surfaces 24 and 36 of the front and back panels, 20 and 32 respectively. Alternatively, the elastic bands 44 and 46 could be attached to an inner surface of the front and back panels, 20 and 32 respectively, if desired. Desirably, the elastic bands 44 and 46 are attached in a semi-stretched condition. By "semi-stretched" it is meant that each of the elastic bands 44 and 46 has been stretched and has not been allowed to fully retract to its original length. It should be noted that one or both of the elastic bands 44 and 46 can be secured to the inner surfaces 22 and 34 of the front and back panels, 20 and 32 respectively, if desired.

Referring again to FIG. 1, the method of attaching the elastic bands 44 and 46 to the stretchable material 10 is shown. The elastic band 44 is unwound from a supply roll 48 and is directed through a nip 50 formed by a pair of rollers 52 and 54. The nip 50 allows the elastic band 44 to be stretched to a greater tension than the original tension that it exhibited while on the supply roll 48. This greater tension can be any value from between 1% to about 2,000%. For example, the tension value can be 25%, 50%, 75%, 100%, 150%, 200%, 300%, etc. higher than the original tension exhibited by the elastic band 44 while on the supply roll 48. This higher tension value created by passing through the nip 50 should be less than the "stretched to stop" value of the elastic band 44.

Still referring to FIG. 1, the elastic band 44 has a first surface 56 which is sprayed with an adhesive 58 from an adhesive applicator 60. The adhesive 58 functions to attach the stretched elastic band 44 to the second web 14. Pressure rolls 62 and 64 function to apply pressure to the stretched elastic band 44 to obtain a secure attachment to the second web 14. It should be noted that other means of attaching and securing the elastic band 44 to the second web 14 can also be employed. Such means include the use of ultrasonics, thermal bonds, heat bonds, pressure bonds, a combination of heat and pressure bonds, or a combination of any of the above. The elastic band 44 can also be secured to the second web 14 by a mechanical attachment, such as by sewing with thread. Other means known to those skilled in the art can also be used to secure the elastic band 44 to the second web 14.

As indicated in FIG. 1, the elastic band 44 is cantilevered outward in the Y-Y direction from the longitudinal edge 26 of the second web 14. By "cantilevered" it is meant that the elastic band 44 projects outward beyond the longitudinal edge 26 and is supported only by that portion of the elastic band 44 that overlaps the second web 14. It should be noted that segments of the longitudinal edge 26 become the distal end 26 of each absorbent article 18, see FIG. 3, once the absorbent article 18 is severed from the continuous first and second webs, 12 and 14.

Still referring to FIG. 1, the elastic band 46 is attached to the first web 12 in a similar fashion as was used to attach the elastic band 44 to the second web 14. The second or other elastic band 46 is unwound from a supply roll 66 and is directed through a nip 68 formed by a pair of rollers 70 and 72. The nip 68 allows the elastic band 46 to be stretched to a greater tension than the original tension that it exhibited while on the supply roll 66. This greater tension can be any value from between 1% to about 2,000%. For example, the tension can be 25%, 50%, 75%, 100%, 150%, 200%, 300%, etc. higher than the original tension. This higher tension value created by passing through the nip 68 should be less than the "stretched to stop" value of the elastic band 46.

Still referring to FIG. 1, the elastic band 46 has a first surface 74 which is sprayed with an adhesive 76 from an adhesive applicator 78. The adhesive 76 functions to attach the stretched elastic band 46 to the first web 12. Pressure rolls 80 and 82 function to apply pressure to the stretched elastic band 46 to obtain a secure attachment to the first web 12. As stated above, other means can be employed for attaching and securing the elastic band 46 to the first web 12. Such means include the use of ultrasonics, thermal bonds, heat bonds, pressure bonds, a combination of heat and pressure bonds, or a combination of any of the above. The elastic band 46 can also be secured to the first web 12 by a mechanical attachment, such as by sewing with thread. Other means known to those skilled in the art can also be used to secure the elastic band 46 to the first web 12.

Like the attachment of the elastic band 44 to the second web 14, the elastic band 46 is attached to the first web 12 in a cantilevered fashion such that it extends outward in the Y-Y from the longitudinal edge 38 of the first web 12. By "cantilevered" it is meant that the elastic band 46 projects outward beyond the longitudinal edge 38 and is supported only by that portion of the elastic band 46 that overlaps the first web 12. It should be noted that segments of the longitudinal edge 38 become the distal end 38 of each absorbent article 18, see FIG. 3, once the absorbent article 18 is severed from the continuous first and second webs, 12 and 14.

Referring now to FIGS. 3 and 4, the elastic band 44 has a first end 84, a second end 86, a first side edge 88 and a second side edge 90. The first end 84 overlaps a portion of the outer surface 24 of the front panel 20, in the Y-Y direction, while the second end 86 is spaced away, in the Y-Y direction, from the distal end 26 of the front panel 20. The elastic band 44 is cantilevered outward, in the Y-Y direction, from the distal end 26. The amount that the elastic band 44 is cantilevered out from the distal end 26 can vary to suit one's particular product design. The elastic band 44 has a width (w) that can range from between about 3 millimeters (mm) to about 150 mm. Desirably, the width (w) of the elastic band 44 ranges from between about 5 mm to about 100 mm. More desirably, the width (w) of the elastic band 44 ranges from between about 10 mm to about 50 mm. Most desirably, the width (w) of the elastic band 44 ranges from between about 12 mm to about 25 mm.

The elastic band 44 can extend outward, In the Y-Y direction, from the front panel 20 a distance of from between 1 millimeter (mm) to a distance equal to about 75% of the width (w) of the elastic band 44. Desirably, the elastic band 44 extends outward from the front panel 20 by a distance that ranges from between about 2 mm to about 75 mm. More desirably, the elastic band 44 extends outward from the front panel 20 by a distance that ranges from between about 3 mm to about 50 mm. Most desirably, the elastic band 44 extends outward from the front panel 20 by a distance of at least about 10 mm.

Likewise, the second elastic band 46 has a first end 92, a second end 94, a first side edge 96 and a second side edge 98. The first end 92 overlaps a portion of the outer surface 36 of the back panel 32, in the Y-Y direction, while the second end 94 is spaced away, in the Y-Y direction, from the distal end 38 of the back panel 32. The elastic band 46 is cantilevered outward, in the Y-Y direction, from the distal end 38. The amount that the elastic band 46 is cantilevered out from the distal end 38 can vary to suit one's particular product design. However, it is advantageous to have the elastic bands 44 and 46 cantilever the same amount from the distal ends, 26 and 38 respectively. The elastic band 46 has a width ($w_1$) that can range from between about 3 millimeters (mm) to about 150 mm. Desirably, the width ($w_1$) of the elastic band 46 ranges from between about 5 mm to about 100 mm. More desirably, the width ($w_1$) of the elastic band 46 ranges from between about 10 mm to about 50 mm. Most desirably, the width ($w_1$) of the elastic band 46 ranges from between about 12 mm to about 25 mm.

The elastic band 46 can extend outward, in the Y-Y direction, from the back panel 32 a distance of from between about 1 millimeter (mm) to a distance equal to about 75% of the width ($w_1$) of the elastic band 46. Desirably, the elastic band 48 extends outward from the back panel 32 by a distance that ranges from between about 2 mm to about 75 mm. More desirably, the elastic band 46 extends outward from the back panel 32 by a distance that ranges from between about 3 mm to about 50 mm. Most desirably, the elastic band 46 extends outward from the back panel 32 by a distance of at least about 10 mm.

Returning to FIG. 3, each of the elastic bands 44 and 46 has a retracted length measured as the distance between the first and second side edges, 88 and 90, and 96 and 98 respectively. The retracted length is measured after the force required to stretch each of the elastic bands 44 and 46 has been removed. The retracted length of each of the elastic bands 44 and 46 can be less than or equal to the retracted length of the front or back panel, 20 or 32 respectively, to which it is attached. Desirably, the retracted length of each of the elastic bands 44 and 46 is less than the retracted length of the front or back panel, 20 or 32 respectively, to which it is attached. When this is the case, each of the elastic bands 44 and 46 will retract to a shorter length than the front or back panel, 20 or 32 respectively, to which it is secured, once the force needed to stretch each of the elastic bands 44 and 46 has been removed. For example, in a small size adult care incontinence undergarment, if each of the front and back panels, 20 and 32 respectively, has a retracted length of about 13 inches (about 330 mm), each of the elastic bands 44 and 46 can have a retracted length of about 12.5 inches (about 318 mm) or less. This difference of about 0.5 inches (about 12 mm) or less means that each of the elastic bands 44 and 46 will provide a snugger or tighter fit around the wearer's torso than the fit provided by the front and back panels, 20 and 32 respectively. Desirably, each of the elastic bands 44 and 46 has a retracted length that is at least 2% less than the retracted length of the panel to which it is secured. More desirably, each of the elastic bands 44 and 46 has a retracted length that is at least 5% less than the retracted length of the panel to which it is secured. Still more desirably, each of the elastic bands 44 and 46 has a retracted length that is at least 10% less than the retracted length of the panel to which it is secured. Most desirably, each of the elastic bands 44 and 46 has a retracted length that is at least 15% less than the retracted length of the panel to which it is secured.

Another way of describing the retracted length of each of the elastic bands 44 and 46 is to mention specific distances. Each of the elastic bands 44 and 46 should have a retracted length that is at least equal to the retracted length of the panel to which it is secured. Desirably, each of the elastic bands 44 and 46 should have a retracted length that is at least about 0.25 inches (about 6 mm) shorter than the retracted length of the panel to which it is secured. More desirably, each of the elastic bands 44 and 46 should have a retracted length that is at least about 0.5 inches (about 12 mm) shorter than the retracted length of the panel to which it is secured. Still more desirably, each of the elastic bands 44 and 46 should have a retracted length that is at least about 0.75 inches (about 19 mm) shorter than the retracted length of the panel to which it is secured. Most desirably, each of the elastic bands 44 and 46 should have a retracted length that is at least about 1 inch (about 25 mm) shorter than the retracted length of the panel to which it is secured. The exact amount by which the retracted length of each of the elastic bands 44 and 46 is shorter than the retracted length of the panel to which it is secured will depend upon various factors including: the distance between the first and second side edges of the two materials, 28 and 30, and 88 and 90 respectively; the type of material from which the front and back panels, 20 and 32 respectively, are formed; the type of material from which the elastic bands 44 and 46 are formed; the elastic tension in each material; the thickness of each material; the overall surface area of each material; etc.

Still referring to FIGS. 3 and 4, each of the elastic bands 44 and 46 is constructed from a non-elastic member 100 having one or more elastic strands 102 secured thereto. The non-elastic member 100 can be formed from natural or synthetic fibers. The non-elastic member 100 can be a woven or nonwoven material. The non-elastic member 100 can be essentially non-stretchable. By "essentially non-stretchable" it is meant that the material will not stretch in any one direction by more than about 5%. The non-elastic member 100 should have a soft feel, be commercially available and be relatively inexpensive. An example of a non-woven material that can be used to form the non-elastic member 100 is polypropylene spunbond. Other materials that can be used to form the non-elastic member 100 include cotton, a bonded carded web, a thermoplastic film, a soft film, a nonwoven net material, etc. Any other material that is known to those skilled in the art can also be used. Furthermore, the non-elastic member 100 can also be a laminate formed from two or more layers.

Alternatively, the elastic bands 44 and 46 could be an elastic nonwoven or an elastic laminate. For example, the elastic bands 44 and 46 could be an elastic nonwoven like meltblown or spunbond urethane. The elastic bands 44 and 46 could also be formed from a material containing a surface treatment like KRATON. KRATON Is a registered trademark of E. I. Du Pont De Nemours & Company having an office at 1007 Market Street, Wilmington, Del. 19898. Furthermore, the elastic bands 44 and 46 could be a stretch bonded laminate, a neck bonded laminate, or any other elastic laminate known to those skilled in the art.

The elastic strands 102 can be formed from LYCRA or KRAYTON. LYCRA and KRAYTON are registered trademarks of E. I. Du Pont De Nemours & Company having an office at 1007 Market Street, Wilmington, Del. 19898. The elastic strands 102 can also be formed from natural rubber or from an elastomeric material, such as a meltblown elastomer. Other elastic materials known to those skilled In the art can also be used.

At least one of the elastic strands 102 in each of the elastic bands 44 and 46 can extend from the first side edge, 88 and 96, of the front and back panels, 20 and 32 respectively, to the second side edge, 90 and 98, of the front and back panels, 20 and 32 respectively. Desirably, all of the elastic strands 102 in each of the elastic bands 44 and 46 will extend from the first side edge, 88 and 96, to the second side edge 90 and 98, as is depicted in FIG. 3. Alternatively, at least one of the elastic strands 102 in each of the elastic bands 44 and 46 does not extend from the first side edge, 88 and 96, of the front and back panels, 20 and 32 respectively, to the second side edge, 90 and 98, of the front and back panels, 20 and 32 respectively. For example, one or more of the elastic strands 102 in each of the elastic bands 44 and 46 can extend over only a portion of the distance located between the first and second side edges, 88 and 90, and 96 and 98 respectively.

It should be noted that the elastic strands 102 can be aligned approximately parallel to one another or be angled or skewed relative to one another. The elastic strands 102 can also be uniformly or randomly spaced apart from one another. The elastic strands 102 can vary in shape, size, configuration, and/or length. The diameter and/or cross-sectional configuration of the elastic strands 102, the decitex (weight in grams per 10,000 meters of each elastic strand 102), and the tension imparted into the elastic strands 102 can all be varied to suit one's particular product needs. The elastic strands 102 can have a round, semi-circular, square, rectangular, oval or some other geometrical cross-sectional configuration. The elastic strands 102 can overlap, intersect or crisscross at least one other elastic strand 102. The various ways of positioning, orienting, and adhering the elastic strands 102 to the non-elastic member 100 are well known to those skilled in the art.

The number of elastic strands 102 can range from 1 to well over 100. The exact number of elastic strands 102 that are present will depend on the width (w) or ($w_1$) of each of the elastic bands, 44 and 46 respectively, the diameter of each elastic strands 102, the arrangement of the elastic strands 102 on the non-elastic member 100, etc. Desirably, from about 2 to about 50 elastic strands 102 are present in each of the elastic bands 44 and 46. More desirably, from about 3 to about 25 elastic strands 102 are present in each of the elastic bands 44 and 46. Most desirably, from about 4 to about 10 elastic strands 102 are present in the elastic bands 44 and 46. In FIGS. 3 and 4, three elastic strands 102 are depicted in each of the elastic bands 44 and 46.

Still referring to FIGS. 3 and 4, one can see that each of the non-elastic members 100 is depicted as being folded in half such that the three elastic strands 102 are located inside the fold. The fold is aligned adjacent to the second ends, 86 and 94, of the elastic bands, 44 and 46 respectively. This structure provides for a smooth, upper edge. Each of the folded non-elastic members 100 will assure that there is not a sharp or abrasive edge that can contact the wearer's skin. It should be noted that the non-elastic member 100 does not have to be folded if one wishes to use a different structure. For example, each of the non-elastic members 100 can be constructed like a sandwich with the three elastic strands 102 being positioned between two outer non-elastic layers.

Returning again to FIGS. 1, 3 and 4, the method also includes securing an absorbent assembly 104 to the front and back panels, 20 and 32 respectively. One will notice in FIG. 1 that each absorbent assembly 104 is secured to the front and back panels, 20 and 32 respectively, after the elastic bands 44 and 46 have been attached to the first and second webs, 12 and 14 respectively. The absorbent assembly 104 includes a liquid pervious bodyside liner 106, a liquid-impervious outer cover 108, and an absorbent 110 positioned therebetween, see FIGS. 3 and 4. A surge layer 112 can be optionally used, which is located between the bodyside liner 106 and the absorbent 110. The surge layer 112 can function to rapidly acquire and temporarily retain body fluid, such as urine, before it can be absorbed into the absorbent 110. Desirably, the surge layer 112 is also capable of wicking body fluid lengthwise and/or widthwise across its surface as well as directing the body fluid downward in a z-direction, toward the absorbent 110.

As depicted in FIG. 3, the absorbent assembly 104 has a first end 114, a second end 116, a first side edge 118 and a second side edge 120. The absorbent assembly 104 is shown secured to the inner surface 22 of the front panel 20 approximate the first end 114 by an attachment 122, see FIG. 4. The absorbent assembly 104 is also secured to the inner surface 34 of the back panel 32 approximate the second end 116 by an attachment 124. Alternatively, the absorbent assembly 104 can be secured to the outer surfaces 24 and 36 of the front and back panels, 20 and 32 respectively, if desired. The absorbent assembly 104 can be secured to the front and back panels, 20 and 32 respectively, after each panel has been stretched a predetermined amount or stretched to stop. By attaching the absorbent assembly 104 to the inner surfaces 22 and 34 of the front and back panels, 20 and 32 respectively, the absorbent assembly 104 is capable of being in direct contact with the wearer's body.

Still referring to FIG. 4, the attachments 122 and 124 can be by various means and can include permanent attachments as well as removable or releasable attachments. Desirably, the attachments 122 and 124 are permanent attachments where they are not designed to be removed without destroying the bond. The attachments 122 and 124 can be formed by using glue, adhesive, ultrasonic bonds, thermal bonds, heat bonds, pressure bonds, heat and pressure bonds, or any other attachment mechanism known to those skilled in the art. The attachments 122 and 124 can also include a mechanical fastener, such as by sewing with thread, using buttons and button holes, using snaps, by employing hook and loop fasteners, etc. A hook and loop fastener is generally considered a releasable attachment One type of hook and loop fastener is VELCRO wherein a hook material is releasably engaged into a loop material. VELCRO is a registered trademark of Velcro USA, Inc. having an office at 406 Brown Avenue, Manchester, N.H. 03103.

The attachments 122 and 124 can be formed along a continuous line or over a surface area having a predetermined length and width. Alternatively, the attachments 122 and 124 can consist of intermittent point bonds that are spaced apart from one another. For example, the intermittent point bonds can be formed by using a hot or cold melt adhesive or by forming ultrasonic bonds. Various bond formations can be used which are known to those skilled in the art. Desirably, the attachments 122 and 124 are formed using intermittent bonds because it allows the elastic material forming the front and back panels, 20 and 32 respectively, to gather the absorbent assembly 104 as the elastic contracts. This gathering feature causes the absorbent assembly 104 to remain in direct contact with the user's body prior to, during and after the time period that the absorbent assembly 104 is being insulted with body fluid.

Returning to FIG. 1, the first and second webs, 12 and 14 respectively, form the front and back panels, 20 and 32 respectively, of the absorbent article 18. The first and second webs, 12 and 14 respectively, are stretched in a direction approximately parallel to the longitudinal centerline X-X before the absorbent assembly 104 is secured to them. The amount of stretch can vary. Optionally, no stretch is required. Desirably, the first and second webs, 12 and 14 respectively, are stretched from between about 10% to about 500%, from a relaxed state, before the absorbent assembly 104 is secured to them. Desirably, the first and second webs, 12 and 14 respectively, are stretched from between about 50% to about 300%, from a relaxed state, before the absorbent assembly 104 is secured to them. More desirably, the first and second webs, 12 and 14 respectively, are stretched from between about 75% to about 270%, from a relaxed state, before the absorbent assembly 104 is secured to them. Most desirably, the first and second webs, 12 and 14 respectively, are stretched from between about 100% to about 250%, from a relaxed state, before the absorbent assembly 104 is secured to them.

Referring to FIG. 3, the front panel 20 extends longitudinally, in the Y-Y direction, beyond the first end 114 of the absorbent assembly 104, and the back panel 32 extends longitudinally beyond the second end 116 of the absorbent assembly 104. In addition, the front and back panels, 20 and 32 respectively, extend laterally, in the X-X direction, beyond the first and second side edges, 118 and 120 respectively, of the absorbent assembly 104. The size and shape of the front and back panels, 20 and 32 respectively, permits them to elastically conform to the torso of the wearer when the absorbent article 18 is being worn while maintaining the absorbent assembly 104 over the fluid discharge area of the body.

Referring again to FIG. 2, when the absorbent assembly 104 is secured to the front and back panels, 20 and 32 respectively, a crotch region 126 is formed. The crotch region 126 separates the front panel 20 from the back panel 32 and is designed to cover the perineum area of the wearer. The crotch region 126 can cover a distance of a few inches in an infant diaper to several inches in an adult incontinence garment. For example, a crotch region 126 in an infant diaper may range from about 2 inches (about 5 centimeters (cm)) to about 10 inches (about 25 cm), while in an adult incontinence garment, the crotch region 126 may range from about 6 inches (about 15 cm) to about 20 inches (about 51 cm).

The absorbent assembly 104 can be stretchable or non-stretchable in relation to the front and back panels, 20 and 32 respectively. Desirably, the absorbent assembly 104 is non-stretchable in relation to the front and back panels, 20 and 32 respectively. By having the absorbent assembly 104 be non-stretchable in relation to the front and back panels, 20 and 32 respectively, it is meant that the absorbent assembly 104 will not stretch appreciably in the longitudinal or transverse directions. The reason for this is that the front and back panels, 20 and 32 respectively, are elastically stretchable so that they can extend and retract to snugly conform to the user's anatomy, especially to his or her torso. The absorbent assembly 104 does not require this degree of extension and retraction. Alternatively, the absorbent assembly 104 could be constructed with a pleated or folded construction, so as to be capable of being expanded in the longitudinal or transverse directions, if expansion of the absorbent assembly 104 is needed. The pleating or folding should occur before the absorbent assembly 104 is secured to the front and back panels, 20 and 32 respectively.

Normally, there is no need to have the absorbent assembly 104 gather as the front and back panels, 20 and 32 respectively, retract. However, the absorbent assembly 104 can be constructed and attached to the front and back panels, 20 and 32 respectively, in a way that will allow the absorbent assembly 104 to be gathered as the front and back panels, 20 and 32 respectively, elastically retract in the transverse X-X direction. In either circumstance, the absorbent assembly 104 should remain positioned over the perineum. As the absorbent assembly 104 receives body fluid and/or excrement discharged by the wearer, it will be displaced outward, away from the user's torso. The attachments 122 and 124 assure that the absorbent assembly 104 covers the perineum but is capable of moving outward away from the torso as additional body fluid is received and retained.

Referring again to FIG. 3, the absorbent assembly 104 also has at least one elastic member 128 positioned adjacent to and aligned approximately parallel to each of the first and second side edges 118 and 120. Each of the elastic members 128 is situated between the bodyside liner 106 and the outer cover 108. Each of the elastic members 128 provides a gasket to hold the side edges 118 and 120 of the absorbent assembly 104 against the user's body. Each of the elastic members 128 can be in the form of an elastic strand, ribbon or strip. Desirably, there are from about 2 to 6 elastic members 128 positioned adjacent to each of the side edges 118 and 120. In FIG. 3, two elastic members 128 are shown positioned adjacent to each of the side edges, 118 and 120 respectively. The elastic members 128 can have a cross-sectional configuration that is round, square, rectangular or any other desired geometrical configuration. The elastic members 128 can be aligned parallel to the Y-Y axis and should extend completely through the crotch region 126. Desirably, the ends of the elastic members 128 will be positioned over a portion of the front and back panels, 20 and 32 respectively.

Still referring to FIGS. 2 and 3, the absorbent article 18 can also include one or more leg elastics 130 and 132 positioned in the front and back panels, 20 and 32 respectively. Each of the leg elastics 130 and 132 is shown consisting of three elastic strands, see FIG. 3, although it should be understood that from 1 to about 10 elastic strands 130 and 132 could be used, if desired. The leg elastics 130 can be positioned between the inner and outer surfaces, 22 and 24 respectively, of the front panel 20. Likewise, the leg elastics 132 can be positioned between the inner and outer surfaces, 34 and 36 respectively, of the back panel 32. Normally, the leg elastics 130 and 132 are aligned approximately parallel to the edges of the front and back panels, 20 and 32 respectively. Such edges are located adjacent to the crotch region 126 of the absorbent assembly 104. The leg elastics 130 and 132 can be uniformly or randomly spaced apart from one another and are normally located within about 0.3 inches (about 0.76 cm) of a pair of leg openings which will be explained shortly.

Figure 5:
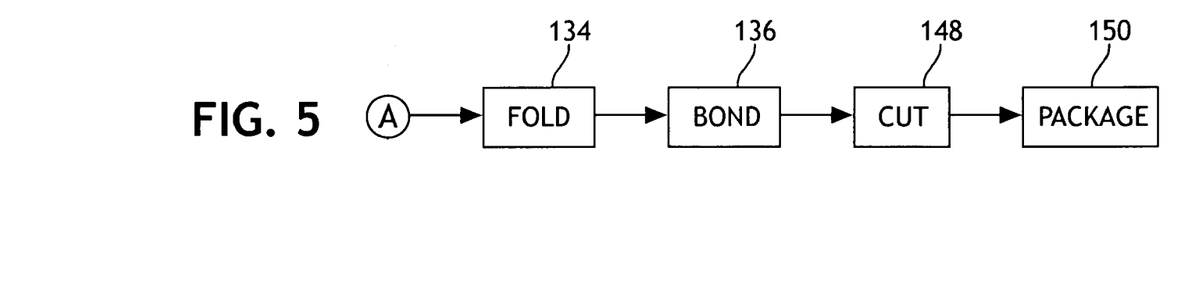
FIG. 5 is a flow diagram of an inline manufacturing method for an absorbent article depicting a folding, a bonding, a cutting and a packaging step.

Referring now to FIG. 5, the method further includes folding the second web 14 along the centerline X-X such that it overlies the first web 12. This action will cause the front panel 20 to be folded over the back panel 32. The folding step is depicted as box 134. During the folding operation, the absorbent assembly 104 is folded at or near the centerline X-X such that the second or outer end 86 of the elastic band 44 is aligned approximately even with the second or outer end 94 of the elastic band 46. If one panel is much larger in size, when measured along the Y-Y axis, then the absorbent assembly 104 will be folded a greater distance away from the centerline X-X. It should also be noted that when only one elastic band is attached to either the front or back panel, 20 or 32 respectively, that after folding, the distal end of the panel without the elastic band should be aligned approximately even with the outer end of the elastic band.

Still referring to FIG. 5, after being folded, the first and second webs, 12 and 14 respectively, are bonded or joined together. The bonding step is depicted as box 136. This bonding occurs at the first and second side edges 28 and 30, and 40 and 42 of the front and back panels, 20 and 32 respectively, as well as at the first and second side edges 88 and 90, and 96 and 98 of the elastic bands 44 and 46. After having been folded, the first side edge 28 of the front panel 20 will be aligned with the first side edge 40 of the back panel 32. Likewise, the second side edge 30 of the front panel 20 will be aligned with the second side edge 42 of the back panel 32. These first and second side edges, 88 and 96, and 90 and 98, can be joined together by a pair of seams 138 and 140, see FIG. 2. The seam 138 secures the first side edge 28 of the front panel 20 and the first side edge 88 of the elastic band 44 to both the first side edge 40 of the back panel 32 and the first side edge 96 of the second elastic band 46. The other seam 140 secures the second side edge 30 of the front panel 20 and the second side edge 90 of the elastic band 44 to both the second side edge 42 of the back panel 32 and the second side edge 98 of the other elastic band 46. After the pair of seams 138 and 140 is formed, the absorbent article 18 will have a waist opening 142 and a pair of leg openings 144 and 146. The leg elastics, 130 and 132, described supra, will surround the leg openings 144 and 146 and provide seals to prevent the escape of body fluid from the absorbent article 18. Likewise, the two elastic bands 44 and 46 will surround the waist opening 142 and create a snug fit against the waist of the wearer. Since the front and back panels, 20 and 32 respectively, are formed from a stretchable elastic material, the pair of leg openings 144 and 146 can expand or retract in size to accommodate the anatomy of the user.

The pair of seams 138 and 140 can be designed to be either permanent seams or tearable seams. The choice will depend on the type of absorbent article 18 being manufactured and how it is designed to be utilized.

Still referring to FIG. 5, each absorbent article 18 has to be cut or severed from the first and second continuous webs, 12 and 14 respectively. The cutting step is depicted as box 148. A good location to sever each adjacent article 18 is at the seams 138 and 140. The seams 138 and 140 can be cut parallel to the Y-Y axis such that sufficient material is present in each of the seams 138 and 140 to insure that they will not prematurely come apart.

It should be noted that a plurality of the absorbent articles 18 can be grouped and packaged for distribution and sale to retailers, who in turn, will sell the absorbent articles 18 to the ultimate customer. The packaging step is depicted as box 150. Various numbers of absorbent articles 18 can be packaged together. For example, a travel package may contain as few as 1 to 3 absorbent articles 18, while an economy package may contain over 100 absorbent articles 18. Today, many manufactures create a plurality of packages each containing various numbers of absorbent articles 18.

Figure 6:
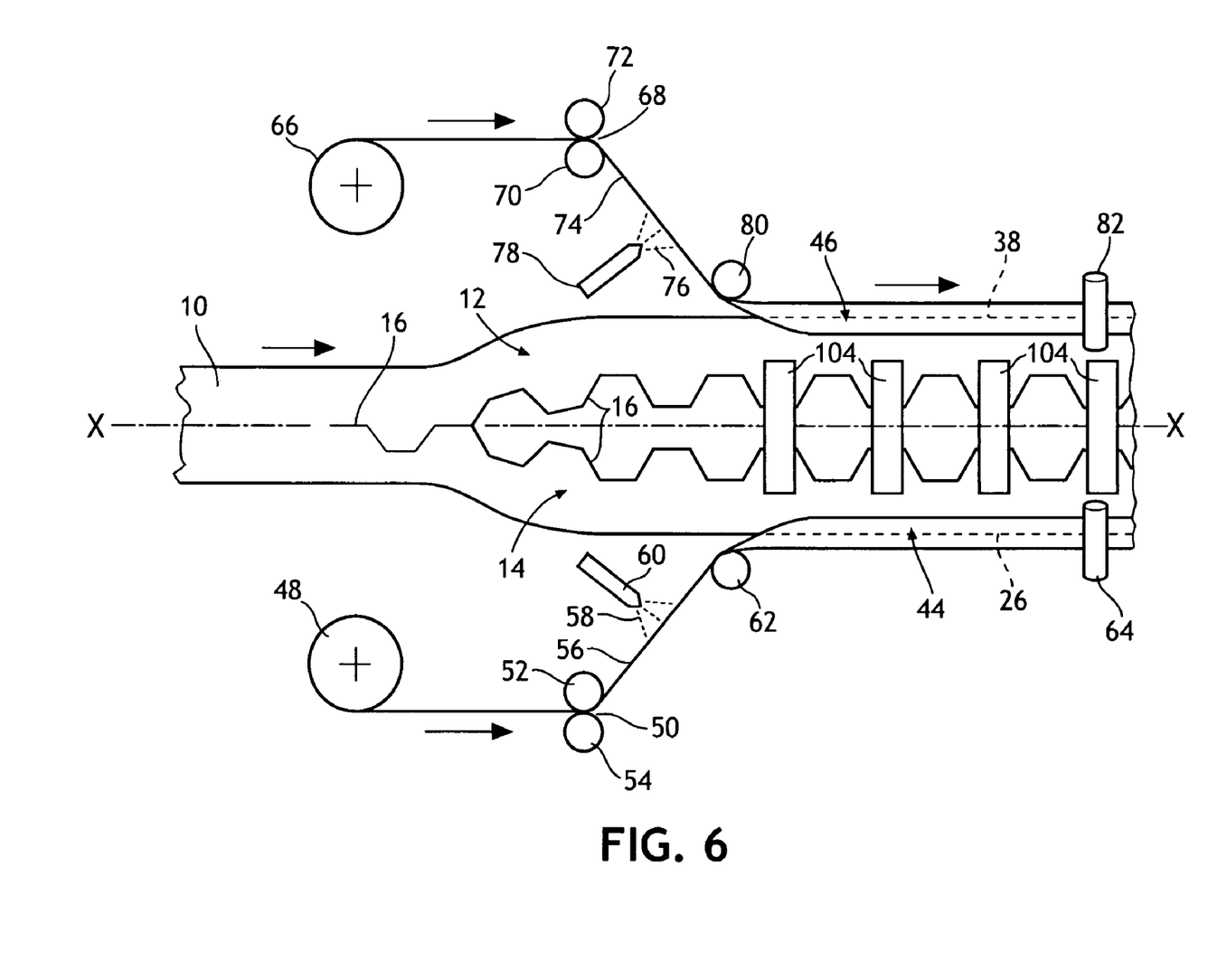
FIG. 6 is a schematic of a portion of the method of forming a waist band on an absorbent article wherein the elastic band is attached to at least one of the front and back panels simultaneous with the securement of an absorbent assembly.
Figure 7:
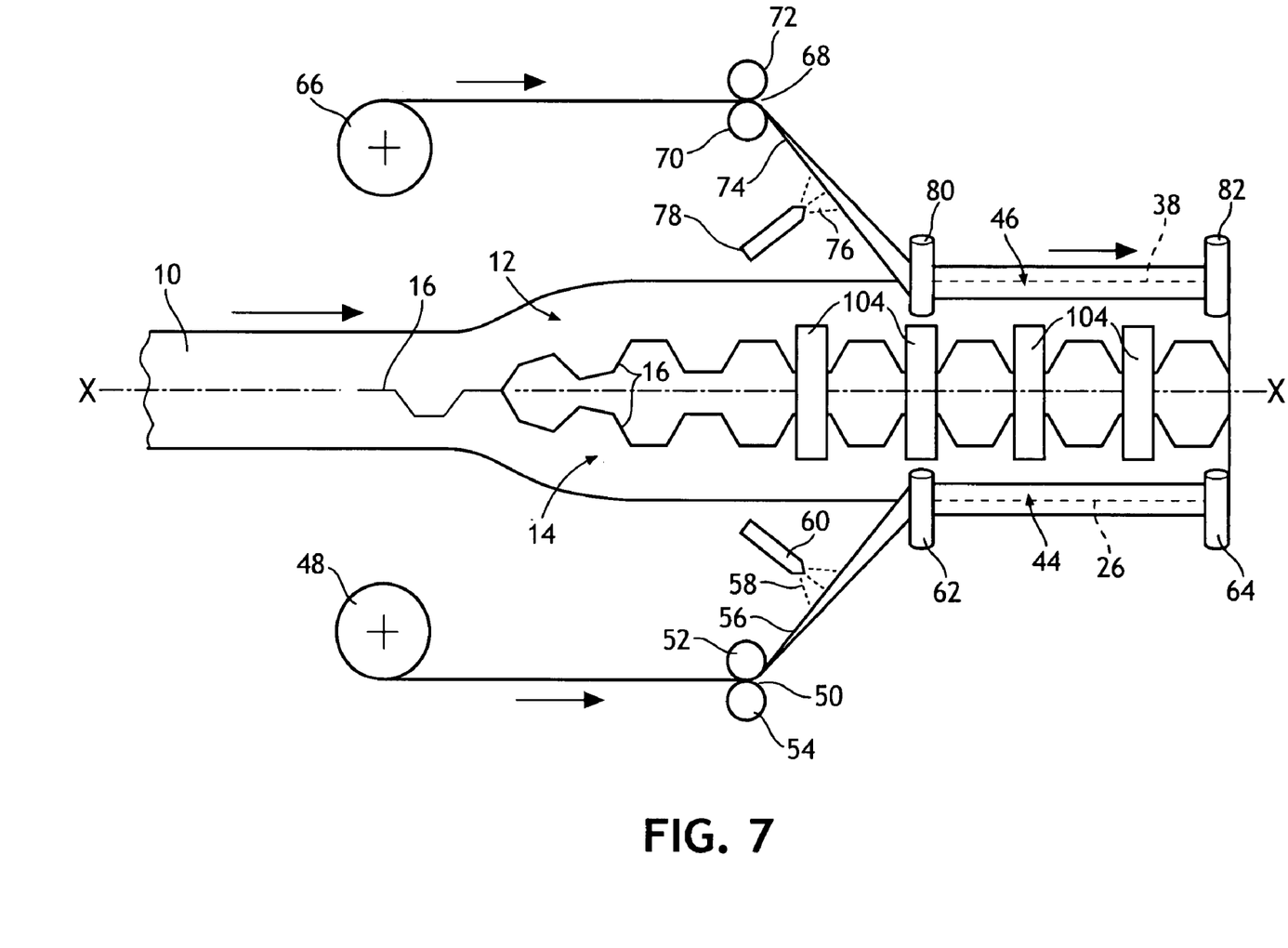
FIG. 7 is a schematic of a portion of the method of forming a waist band on an absorbent article wherein the elastic band is attached to at least one of the front and back panels after the securement of an absorbent assembly.

Referring now to FIGS. 6 and 7, two alternative embodiments are shown which differ from FIG. 1 only in the timing of attaching the elastic bands 44 and 46 relative to the securement of the absorbent assembly 104 to the first and second webs, 12 and 14 respectively. The apparatus and webs shown in FIGS. 6 and 7 have been described using the same numerals as were used in FIG. 1, for the purpose of clarity. In FIG. 6, at least one of the elastic bands 44 and 46, and desirably both elastic bands 44 and 46, are attached to the second and first webs, 14 and 12 respectively, at the same time as the absorbent assembly 104 is secured to the first and second webs 12 and 14 respectively. As noted above, the first web 12 forms the front panel 20 while the second web 14 forms the back panel 32. This simultaneous attachment may shorten the overall length of the equipment needed to perform the product assembly.

Lastly, in FIG. 7, the elastic bands, 44 and 46, are attached to the second and first webs, 14 and 12 respectively, at a later time or after the absorbent assembly 104 is secured to the first and second webs 12 and 14 respectively. Some manufacturers may find it easier to secure the absorbent assembly 104 in place before attaching the elastic bands 44 and 46. This sequential operation may lengthen the overall length of the equipment needed to perform the product assembly when compared to that shown in FIG. 6.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A method of forming a waist band on an absorbent article comprising;
   a) forming a stretchable first web having a distal end;
   b) forming a stretchable second web having a distal end, said second web being spaced apart from said first web;
   c) attaching an elastic band to one of said first and second webs, said elastic band having an outer end, and said elastic band being cantilevered outward from said distal end of said web to which it is attached;
   d) securing an absorbent assembly to said first and second webs, said absorbent assembly including a liquid pervious bodyside liner, a liquid-impervious outer cover, and an absorbent positioned therebetween;
   e) folding said web without said elastic band over said web with said elastic band so that said distal end of said web without said elastic band is aligned approximately even with said outer end of said elastic band;
   f) bonding said first web, said second web and said elastic band together by a pair of seams to form a waist opening and a pair of leg openings;
   g) cutting said first web, said second web and said elastic band at said pair of seams to form an absorbent article, said absorbent article having a front panel with first and second side edges and having a retracted length measured between said first and second side edges, a back panel with first and second side edges and having a retracted length measured between said first and second side edges, and said elastic band having first and second side edges and having a retracted length that is less than said retracted length of said panel to which it is secured.

2. The method of claim 1 wherein at least one of said first and second webs is stretched to stop before said elastic band is attached thereto.

3. The method of claim 2 wherein said elastic band is stretched while being attached to said web.

4. The method of claim 3 wherein said elastic band is stretched to a greater extent than said web to which it is attached.

5. The method of claim 4 wherein said elastic band is stretched to a stop position and then partially relaxed prior to attachment to one of said webs.

6. The method of claim 1 wherein said elastic band is secured to one of said webs before said absorbent assembly is secured to both said first and second webs.

7. The method of claim 1 wherein said elastic band is attached to one of said webs after said absorbent assembly is secured to both said first and second webs.

8. The method of claim 1 wherein said elastic band is attached to one of said webs at the same time said absorbent assembly is secured to both said first and second webs.

9. The method of claim 1 wherein each of said first and second webs is stretched from between about 10% to about 500% prior to having said absorbent assembly attached to them.

10. A method of forming a waist band on an absorbent article comprising:
   a) forming a stretchable first web having a distal end;
   b) forming a stretchable second web having a distal end, said second web being spaced apart from said first web;
   c) attaching an elastic band to said first web after said first web has been stretched from between about 10% to about 500%, said elastic band having an outer end; and said elastic band being cantilevered outward from said distal end of said first web;
   d) securing an absorbent assembly to said first and second webs, said absorbent assembly including a liquid pervious bodyside liner, a liquid-impervious outer cover, and an absorbent positioned therebetween, said absorbent assembly being positioned between said distal ends of said first and second webs;
   e) folding said second web over said first web so that said distal end of said second web is aligned approximately even with said outer end of said elastic band;
   f) bonding said first web, said second web and said elastic band together by a pair of seams to form a waist opening and a pair of leg openings; and
   g) cutting said first web, said second web and said elastic band at said pair of seams to form an absorbent article, said absorbent article having a front panel with first and second side edges and having a retracted length measured between said first and second side edges, a back panel with first and second side edges and having a refracted length measured between said first and second side edges, and said elastic band having first and second side edges and having a retracted length that is less than said refracted length of said front panel to which it is secured.

11. The method of claim 10 wherein said elastic band extends outward beyond said distal edge of said front panel by a distance of from between about 1 millimeter to about 75 millimeters.

12. The method of claim 11 wherein said elastic band extends outward beyond said distal edge of said front panel by a distance of at least about 10 millimeters.

13. The method of claim 10 wherein said front panel and said elastic band has a force of retraction, and said force of retraction in said elastic band is greater than said force of retraction in said front panel.

14. The method of claim 10 wherein each of said first and second webs is stretched from between about 50% to about 300% prior to having said absorbent assembly attached to them.

15. The method of claim 10 wherein each of said first and second webs is stretched from between about 75% to about 270% prior to having said absorbent assembly attached to them.

16. A method of forming a waist band on an absorbent article comprising:
   a) forming a stretchable first web having a distal end;
   b) forming a stretchable second web having a distal end and an outside surface, said second web being spaced apart from said first web;
   c) attaching an elastic band to said outside surface of said second web after said second web has been stretched from between about 50% to about 300%, said elastic band having an outer end, and said elastic band being cantilevered outward from said distal end of said second web;
   d) securing an absorbent assembly to said first and second webs, said absorbent assembly including a liquid pervious bodyside liner, a liquid-impervious outer cover, and an absorbent positioned therebetween, said absorbent assembly being positioned between said distal ends of said first and second webs;
   e) folding said second web over said first web so that said outer end of said elastic band is aligned approximately even with said distal end of said first web;
   f) bonding said first web, said second web and said elastic band together by a pair of seams to form a waist opening and a pair of leg openings; and
   g) cutting said first web, said second web and said elastic band at said pair of seams to form an absorbent article, said absorbent article having a front panel with first and second side edges and having a retracted length measured between said first and second side edges, a back panel with first and second side edges and having a retracted length measured between said first and second side edges, and said elastic band having first and second side edges and having a retracted length that is less than said retracted length of said back panel to which it is secured.

17. The method of claim 16 wherein said elastic band extends outward beyond said distal edge of said back panel by a distance of from between about 1 millimeter to about 75 millimeters.

18. The method of claim 17 wherein said elastic band has a retracted length that Is at least 2% less than the retracted length of said back panel.

19. The method of claim 16 wherein said absorbent assembly is secured to both said first and second webs before said elastic band is secured to said second web.

20. The method of claim 16 wherein said second web is stretched from between about 50% to about 300% prior to having said elastic band attached thereto.

* * * * *